United States Patent [19]

Labat

[11] Patent Number: 4,847,420
[45] Date of Patent: Jul. 11, 1989

[54] NEW HYDROXY-THIA-ALKENES, AND PROCESSES FOR THEIR PREPARATION AND USE

[75] Inventor: Yves Labat, Pau, France

[73] Assignee: Societe Nationale Elf Aquitaine, France

[21] Appl. No.: 88,810

[22] Filed: Aug. 24, 1987

Related U.S. Application Data

[63] Continuation-in-part of Ser. No. 779,506, Sep. 24, 1985, abandoned.

[30] Foreign Application Priority Data

Sep. 25, 1984 [FR] France .................. 84 14665

[51] Int. Cl.[4] .................. C07C 148/00; C08G 75/00
[52] U.S. Cl. .................. 568/55; 528/396
[58] Field of Search .................. 568/55; 528/376

[56] References Cited

U.S. PATENT DOCUMENTS

| | | | |
|---|---|---|---|
| 3,591,475 | 7/1971 | Griebaum et al. | 568/59 |
| 3,708,543 | 1/1973 | Hickner et al. | 568/55 |
| 3,729,518 | 4/1973 | Lepper et al. | 568/55 |
| 3,763,116 | 10/1973 | Kleiner et al. | 568/55 |
| 4,086,278 | 4/1978 | Hirsch | 568/55 |

FOREIGN PATENT DOCUMENTS 441457 10/1934 United Kingdom .

*Primary Examiner*—Mary E. Ceperley
*Attorney, Agent, or Firm*—Ostrolenk, Faber, Gerb & Soffen

[57] ABSTRACT

New unsaturated alcohol-thioether, in which a double bond is located in the beta position to the S atom, in an aliphatic chain which can repeat. The compounds are generally of the formula

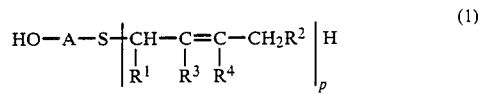

(1)

In this formula, A is a branched or unbranched aliphatic chain which may be substituted or unsubstituted, and preferably contains from 2–6 carbon atoms; $R^1$, $R^3$ and $R^4$ may be the same or different, and are aliphatic groups and/or hydrogen atoms; $R^2$ is an aliphatic group, hydrogen, alkylene, or a bond and p gives the degree of polymerization of the beta-unsaturated aliphatic chain.

These compounds may be prepared by the reaction of a mercapto-alcohol with a conjugated diene in the presence of a free radical catalyst.

10 Claims, No Drawings

NEW HYDROXY-THIA-ALKENES, AND PROCESSES FOR THEIR PREPARATION AND USE

This application is a continuation-in-part of U.S. application Ser. No. 779,506, filed Sept. 24, 1985 now abandoned.

The present invention relates to a new type of hydroxy-thia-alkene, that is aliphatic alcohol-thioethers, having a chain which comprises one or more double bonds. These compounds are useful in the manufacture of polymeric products having unsaturated thioether units or sidechains. Unsaturated polymers having thioether units on their chain are of particular interest in the manufacture of polysulphides intended for the preparation of mastics, jointing compounds and the like. A process of preparation of the aliphatic alcohol thioether compounds also forms part of the invention.

Alcohol-thioethers having a double bond at the end of the chain, of the general form $HO-CH_2-CH_2-S-PCH=CH_2I$, in which P is an alkylene group comprising 4 to 6 carbon atoms, particularly 1-hydroxy-3-thia-nonene-8, $HO(CH_2)_2-S-(CH_2)_4-CH=CH_2$, are known and used. The preparation of this compound requires the use of hexadiane-1,5 and mercapto-ethanol to effect the reaction $$HO-C_2H_4-SH + CH_2=CH-CH_2-CH_2-CH=CH_2 \longrightarrow$$
$$HO-C_2H_4-S(CH_2)_4-CH=CH_2$$

Hexadiene-1,5 is a relatively expensive hydrocarbon and the above reaction takes place with a yield of unsaturated product, which, in practice, does not exceed 80%.

The present invention provides a substantial advance in the art mentioned above. It achieves the synthesis of a new type of unsaturated alcohol-thioether, the yield of unsaturated products of which is much improved. The preparation of these products is practically quantitative and allows the use of starting materials which are much more accessible than those used in the prior art. This improved process allows the preparation of compounds having a chain which can comprise a plurality of double bonds.

The invention is based upon the quite astonishing discovery that conjugated dienes react with mercapto-alcohols with higher yields of unsaturated products than when using non-conjugated dienes. Thus, it is found that hexadiene-2,4 combines with mercaptoethanol with a yield of unsaturated products well exceeding prior art yield using hexadiene-1,5.

In accordance with the instant invention, a mercapto-alcohol is reacted with a conjugated diene in the presence of a free radical catalyst to produce alcohol; thioethers.

Thus the dienes used according to the invention correspond to the formula

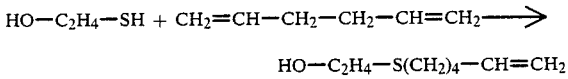

where $R^1$ $R^4$ are aliphatic groups, the same or different, and/or hydrogen atoms. The simplest compound, but also the most economical, is butadiene, that is the diene in which all the symbols $R^1$ to $R^4$ represent hydrogen atoms. Another very interesting diene is isoprene, namely 2-methyl-butadiene-1,3, in which $R^1$, $R^2$ and $R^4$ are H, while $R^3$ is methyl; the branching constituted by this can make advantageous modifications to the properties of the products made from the corresponding alcohol-thioethers.

Other dienes suitable for carrying out the invention include but are not limited to piperylene, namely pentadiene-1,3, 2-ethyl-butadiene-1,3, hexadiene1,3 or 2,4-octadiene-1,3 or 3,5, limonene etc.

Various mercapto-alcohols are suitable for carrying out the invention. To simplify, they are designated here by the general formula HO—A—SH, where A is a branched or unbranched aliphatic chain which may be substituted or unsubstituted, and preferably is comprised of about 1–12 carbon atoms. Useful mercaptoalcohols include but are not limited to straight-chain compounds ranging from mercapto-methanol to a mercaptolauryl alcohol. Certain preferred species include the mercapto-ethyl, propyl, isopropyl, butyl, isobutyl, tertiary butyl, alcohols, etc.

Free radical catalysts are well known and only some of them are mentioned here: azo-bisisobutyronitrile, benzoyl-peroxide, tert.butylperbernzoate, lauroyl-peroxide, isobutyryl peroxide, tert.butyl-peroxyacetate, di-cumyl-peroxide, paramethane-hydroxyperoxide. Photochemical techniques can also be used.

The temperature at which the diene combines most advantageously with the mercapto-alcohol depends upon the nature of the reactants and that of the catalysts employed. It is generally in the range from 0° to 100° C. and preferably from 50° to 90° C. The reactant temperature selected should of course be lower than the temperature of decomposition of the catalyst or any of the reactants.

An important factor in the new process is the molar proportion of the diene used with respect to the mercapto-alcohol. It appears in practice that depending upon the molar ratio of diene to mercapto-alcohol, a range of unsaturated alcohol-thioethers can be obtained, where the chain comprises the residue of one or several molecules of the diene per molecule of mercapto-alcohol. This is one of the surprising characteristics of the invention, which produces a very interesting result, in that it becomes possible to prepare useful mixtures of unsaturated compounds. For difunctional compounds, compositions of different unsaturated alcohol-thioethers can thus be synthesized as indicated below. Preferably molar ratios of diene to mercapto-alcohol range from about 1:1 to about 10:1, the preferred ratios being from about 1.5:1 to 6:1.

The new unsaturated alcohol-thioethers according to the invention can be represented diagrammatically by the general formula:

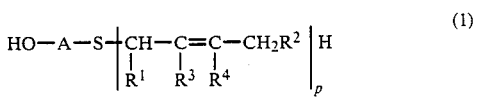 (1)

In this formula, A is a branched or unbranched aliphatic chain which may be substituted or unsubstituted, and most preferably contains from 2–6 carbon atoms; $R^1$, $R^3$ and $R^4$ may be the same or different, and are aliphatic groups and/or hydrogen atoms; $R^2$ may be an aliphatic group, hydrogen, an alkylene or a bond and the $CH_2R^2$ moiety may be divalent and capable of bonding an additional beta-unsaturated aliphatic chain; and p gives the degree of polymerization of the beta-unsaturated aliphatic chain and preferably is not less than 2. This coefficient tends to vary with the diene-mercapto-alcohol ratio mentioned above. Preferably, $R^3$ and $R^4$ are both hydrogen and $R^2$ is either hydrogen or a straight-chain alkyl group of from 1 to 6 carbon atoms. It is preferred that $R^1$ be a moiety having less than 6 carbon atoms (especially less than 5), depending on the nature of the diene used.

What is disclosed above is illustrated below by the case of butadiene, reacting by way of example with mercapto-ethanol; the reaction of one molecule of the former with one of the latter is illustrated below:

   (2)

1-hydroxy-3-thia-heptene-5 (Hereinafter "HTH")

This composition is designated below by the abbreviation "HTH"; it corresponds to the formula (1) in which $A=(CH_2)$, $R^1$, $R^3$ and $R^4$ are all $=R^2$ is a bond and $p=1$.

The second compound, which forms alongside the foregoing, particularly, when the number of moles of butadiene exceeds 2 per 1 of mercapto-ethanol is:

$HOCH_2CH_2S-CH_2-CH=CH-CH_2-CH_2-CH=CH-CH_3$  (3)

1-hydroxy-3-thia-undecadiene-5,9 (HTU)

This results from the addition of 1 mole of butadiene to the foregoing compound HTH; A, $R^1$, $R^2$, $R^3$ and $R^4$ are the same as above, but $p=2$.

A third series of unsaturated alcohol-thioethers forms in the reaction according to the invention, particularly when there are more than 3 moles of butadiene per mole of mercapto-ethanol. These are products containing more than 2 double bonds for instance:

$HOCH_2CH_2S-CH_2-CH=CH-CH_2-CH_2-CH=CH-CH_2-CH_2-CH=CH-CH_3$ (HTP)  (4)

1-hydroxy-3-thia-pentadecatriene-5,9,13

This triene or its isomers form in increasing proportions when the butadiene/mercapto-ethanol ratio increases, particularly above 3.

Isomers of the three compounds exist, but it can be confirmed that the structure of the above products largely predominates. Thus, there are, in particular, isomers with vinyl termination identified by NMR analysis such as:

$HO-(CH_2)_2-S-CH_2-CH_2-CH=CH_2$ about 5% with respect to HTH

 about 20% with respect to HTU

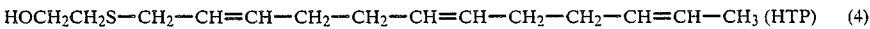 in admixture with HTP.

HTH, HTU and HTP can be separated after distillation of mixtures with their isomers. This can be carried out particularly under the following conditions:

|  | Temperature °C. Vacuum |
|---|---|
| HTH | 70 1 mm Hg |
| HTU | 105 1 mm Hg |
| HTP | 1750.7 mm Hg |

This variety of structure of the alcohol-thioethers which can be obtained according to the invention allows variation in the properties of the products of use of these compounds. For this, the invention provides modification of the diene/mercapto-alcohol molar ratio and, if required, separation of the products obtained, as mentioned above, although use of the crude products constitutes an interesting embodiment.

With other dienes than butadiene, matters proceed in the same fashion, but naturally the number of possible isomers is greater. By way of example, the first compound, 1-hydroxyl-3-thia-4-ethyl-nonene-5, is mentioned below:

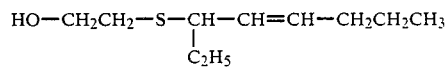

which is obtained from octadiene-3,5 and mercaptoethanol; referring to formula (1), this represents $A=(CH_2)_2$, $R^1=C_2H_5$, $R^3$ and $R^4 =H$, $R^2 =CH_2CH_3$, $p=1$.

The non-limitative Examples which follow illustrate the invention.

EXAMPLE 1

6,458 g of mercapto-ethanol $HO-CH_2-CH_2-SH$, namely 82.8 moles, 6,707 g of butadiene, $CH_2=CH-CH=CH_2$, namely 124. 2 moles, and 150 g azobisisobutyronitrile as catalysts are introduced into a 20-litre autoclave provided with an agitator and a thermostat. Thus, the butadiene/mercaptoethanol molar ratio=1.5. This mixture is heated to 80° C. for 10 hours, after which the remaining butadiene is eliminated.

The 12,744 g of reaction mixture are composed of:
70% or 67 moles of HTH (abbreviation adopted on the preceding pages),
20.5% or 13.8 moles of HTU,
4% or 2 moles of HTP
5.5% of others.

The yield with respect to the mercapto-ethanol is practically quantitative. The reaction mixture obtained contains about 9 unsaturated functions an 6.6 alcohol functions per kg of product, confirmed by NMR analyses and chemical analysis. These unsaturated functions are totally reactive vis-a-vis compounds with a mercaptan function.

EXAMPLE 2

Operation is as in Example 1, but with the following quantities of reactants: 3,300 g of mercapto-propanol or 35.8 moles, 5,730 g of butadiene or 106 moles, 150 g azobisisobutyronitrile. The butadiene/mercapto-propanol molar ratio=2.95.

The reaction mixture obtained contains about 10.2 unsaturated functions and 6.8 alcohol functions per kg of product.

EXAMPLE 3

Comparative tests with a non-conjugated diene

The operations of Example 1 are repeated, but the butadiene is replaced with the same number of moles of hexadiene-1,5. The 1-hydroxy-3-thia-nonene-8 (designated by the initials HTN in the following part of the description) is principally obtained. But the yield with respect to the mercapto-ethanol is only 80%.

EXAMPLES 4 TO 8

Following the technique of Example 1, a series of preparations with increasing butadiene/mercapto-ethanol molar ratios are effected. The conversion and yield are calculated with respect to the mercapto-ethanol.

It can be seen that the conversions range from 93% to 98.5%. The inventive idea is confirmed by the fact that the content of heavier products increases with the excess of butadiene used. The last three horizontal lines of the Table below show clearly that, by varying the excess of butadiene, the composition of the alcohol-thio-ethers can be modified profoundly.

TABLE

| Examples | 4 | 5 | 6 | 7 | 8 |
|---|---|---|---|---|---|
| Molar ratio Butadiene/mercapto-ethanol | 1.5 | 3 | 3 | 6 | 6 |
| Procedure (*) | D | D | C | D | C |
| Conversion % | 98.5 | 98 | 95 | 98.4 | 93 |
| Yield % HTH | 81.7 | 56 | 51 | 46 | 32 |
| HTU | 12 | 25 | 26.7 | 25.6 | 25.7 |
| Composition % HTH | 75.3 | 40.7 | 36 | 27.5 | 19.7 |
| HTU | 15.8 | 25 | 26.7 | 21.5 | 22.1 |
| Heavy Products | 9 | 34.3 | 37 | 51 | 58.2 |

(*) D = discontinuous; C = continuous

What is claimed:

1. A process for preparing an unsaturated alcohol thioether by reacting, in the presence of a catalytic amount of a free radical catalyst, one mol of a mercapto-alcohol HO—A—SH, wherein A is a branched or unbranched alkylene chain, with at least about one mol of a $C_4$ to $C_{10}$ conjugated diene of the formula:

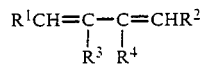

wherein $R^1$, $R^2$, $R^3$ and $R^4$ may be the same or different and individually are hydrogen or alkyl, wherein an unsaturated alcohol thioether is produced having the formula:

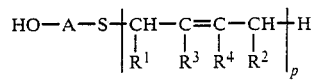

wherein p denotes the degree of polymerization of the moiety:

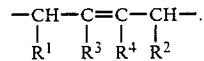

2. The process according to claim 1, wherein $R^3$ and $R^4$ are hydrogen, $R^2$ is hydrogen or a straight chain alkyl group of from 1 to 6 carbon atoms, and $R^1$ is a moiety of less than 6 carbon atoms.

3. The process according to claim 1, wherein p is at least 2 and $R^1$ is a moiety of less than 5 carbon atoms.

4. The process according to claim 1, wherein at least two moles of each diene are employed per mole of mercapto-alcohol.

5. The process according to claim 1, wherein 1 to 6 moles of said diene are employed per mole of mercapto-alcohol.

6. The process according to claim 1, wherein the free radical catalyst is azo-bis-isobutyronitrile, benzoyl-peroxide, tert.butyl-perbenzoate, lauroyl-peroxide, isobutyryl-peroxide, tert.butyl-peroxyacetate, di-cumylperoxide or para-methane-hydroxy-peroxide, and the reaction is carried out at a temperature of 50° to 90° C.

7. The process according to claim 1, wherein the reaction is carried out at a temperature of 0° to 100° C.

8. The process according to claim 1, wherein the diene is butadiene.

9. The process according to claim 1, wherein the diene is selected from the group consisting of isoprene, pentadiene-1,3, 2-ethyl-butadiene-1,3, hexadiene-1,3 or 2,4, and octadiene-1,3 or 3,5.

10. The process of claim 1, wherein A is $C_{2-6}$ alkylene.